US006827931B1

(12) United States Patent
Donovan

(10) Patent No.: US 6,827,931 B1
(45) Date of Patent: Dec. 7, 2004

(54) METHOD FOR TREATING ENDOCRINE DISORDERS

(75) Inventor: Stephen Donovan, Capistrano Beach, CA (US)

(73) Assignee: Allergan, Inc., Irvine, CA (US)

(*) Notice: Subject to any disclaimer, the term of this patent is extended or adjusted under 35 U.S.C. 154(b) by 743 days.

(21) Appl. No.: 09/692,811

(22) Filed: Oct. 20, 2000

(51) Int. Cl.[7] ......................... A61K 38/48; A61K 39/08

(52) U.S. Cl. .................. 424/94.63; 424/94.1; 424/94.6; 424/236.1; 424/239.1; 424/247.1; 512/12; 512/2

(58) Field of Search ............................ 424/94.63, 94.6, 424/94.5, 94.1, 234.1, 247.1, 239.1, 236.1, 237.1; 514/2, 12

(56) References Cited

U.S. PATENT DOCUMENTS

| | | | |
|---|---|---|---|
| 5,989,545 A | 11/1999 | Foster et al. | 424/183.1 |
| 6,113,915 A | 9/2000 | Aoki et al. | 424/236.1 |

FOREIGN PATENT DOCUMENTS

| | | |
|---|---|---|
| EP | 1 005 867 A2 | 6/2000 |
| WO | PCT/US99/17880 | 2/2000 |
| WO | WO 01/41790 A1 | 6/2001 |

OTHER PUBLICATIONS

Van de Kar et al. Alterations in 8–hydroxy–2–(dipropylamino)tetralin–induced neuroendocrine responses after 5, 7–dihydroxytrypatamine–induced denervation of serotonergic neurons. 1998. J. Pharmacology and Experimental Therapeutics 286(1), 256–262.*

D. Andrews Pituitary adenomas. 1997. Current Opinion in Oncology 9(1), 55–60.*

Jacobsson et al. Botulinum neurotoxin F, a VAMP specific endopeptidase inhibits Ca2+ stimulated GH secretion from rat pituitary cells. 1997. Regulatory Peptides 71 37–44.*

Aoki K. R., *Preclinical Update on BOTOX (Botulinum Toxin Type A)–Purified Neurotoxin Complex Relative to Other Botulinum Toxin Preparations*, Eur J. Neur 1999, 6 (suppl 4):S3–S10.

Bejjani, B.P., et al., *Bilateral Subthalamic Stimulation for Parkinson's Disease by Using Three–Dimensional Stereotactic Magnetic Resonance Imaging and Electrophysiological Guidance*, J Neurosurg 92(4);615–25:2000.

Bellezza D., et al., *Stereotactic Interstitial Brachytherapy*, in Gildenberg P.L. et al., *Textbook of Stereotactic and Functional Neurosurgery*, Chapter 66, pp. 577–580, McGraw–Hill (1998).

Bigalke H., et al., *Botulinum A Neurotoxin Inhibits Non–Cholinergic Synaptic Transmission in Mouse Spinal Cord Neurons in Culture*, Brain Research 360;318–324:1985.

Bigalke H., et al., *Tetanus Toxin and Botulinum A Toxin Inhibit Release and Uptake of Various Transmitters, as Studied with Particulate Preparations From Rat Brain and Spinal Cord*, Naunyn–Schmiedeberg's Arch Pharmacol 316;244–251:1981.

Billet S., et al., *Cholinergic Projections to the Visual Thalamus and Superior Colliculus*, Brain Res. 847;121–123:1999.

Blake C.A. et al., *Effects of Hypothalamic Deafferentation and Ovarian Steroids on Pituitary Responsiveness to LH–RH in Female Rats*. In Gual and Rosemberg, eds, *Hypothalamic Hypophysiotropic Hormones*. Excerpta Medica, Amsterdam, 1973, pp. 33–38.

Blake C.A. et al., *Localization of the Inhibitory Actions of Estrogen and Nicotine on Release of Luteinizing Hormone in Rats*, Neuroendocrinology 16: 22–35,1974.

Blake C.A., et al., *Nicotine Delays the Ovulatory Surge of Luteinizing Hormone in the Rat*, Proc Soc Exp Biol Med 141: 1014–1016,1972.

Blake C.A., *Parallelism and Divergence in Luteinizing and Follicle Stimulating Hormone Release in Nicotine–Treated Rats*, Proc Soc Exp Biol Med 145: 716–720, 1974.

Brem, H. et al., *The Safety of Interstitial Chemotherapy with BCNU–Loaded Polymer Followed by Radiation Therapy in the Treatment of Newly Diagnosed Malignant Gliomas: Phase I Trial*, J Neuro–Oncology 26:111–123:1995.

Brem, H., et al, *Placebo–Controlled Trial of Safety and Efficacy of Intraoperative Controlled Delivery by Biodegradable Polymers of Chemotherapy for Recurrent Gliomas*, Lancet 345;1008–1012:1995.

Fiorindo R.P. et al., *Evidence for a Cholinergic Component in the Neuroendocrine Control of Luteinizing Hormone Secretion*, Neuroendocrinology 18: pp 322–332,1975.

Fung L. K. et al., *Pharmacokinetics of Interstitial Delivery of Carmustine 4–Hydroperoxycyclophosphamide and Paclitaxel From a Biodegradable Polymer Implant in the Monkey Brain*, Cancer Research 58;672–684:1998.

Gaspar, et al., *Permanent $^{125}$I Implants for Recurrent Malignant Gliomas*, Int J Radiation Oncology Biol Phys 43(5);977–982:1999.

Habermann E., et al., *Tetanus Toxin and Botulinum A and C Neurotoxins Inhibit Noradrenaline Release From Cultured Mouse Brain*, J Neurochem 51(2);522–527:1988.

Habermann E., *Inhibition by Tetanus and Botulinum A Toxin of the release of [$^3$H]Noradrenaline and [$^3$H]GABA From Rat Brain Homogenate*, Experientia 44;224–226:1988.

Hunter, S., *Stereotactic Hypothalamotomy*, chapter 153, pp. 1507–1517 of *Textbook of Stereotactic and Functional Neurosurgery*, edited by Gildenberg P.L. et al., McGraw–Hill (1998).

(List continued on next page.)

*Primary Examiner*—Gabriele Bugaisky
(74) *Attorney, Agent, or Firm*—Martin A. Voet; Robert J. Baran; Carlos A. Fisher

(57) ABSTRACT

Methods for treating endocrine disorders and for inhibiting gametogenesis by intracranial administration to a human patient of a therapeutically effective amount of a neurotoxin, such as a botulinum toxin type A.

17 Claims, No Drawings

OTHER PUBLICATIONS

Kanematsu S. et al., *Inhibition of the Progesterone–Advanced LH Surge at Proestrus*, Proc Soc Exp Biol Med 143: 1183–5,1973.

Koller, W.C. et al., *Surgical Treatment of Parkinson's Disease*, J Neurol Sci 167;1–10:1999.

Libertun C. et al., *Blockade of the Postorchidectomy Increase in Gonadotropin by Implants of Atropine into the Hypothalamus*, Proc Soc Exp Biol Med 152: 143–146, 1976.

Lindsay K.W. et al., *Neurology and Neurosurgery Illustrated*, pp. 303 and 332 1997 Philadelphia:Churchill Livingstone.

Marjama–Jyons, J., et al., *Tremor–Predominant Parkinson's Disease*, Drugs & Aging 16(4);273–278:2000.

Monti J.M. et al., *Inhibition of Ovarian Compensatory Hypertrophy by Implants of Atropine in the Hypothalamus*, Experientia 26: 1263–1264,1970.

Moyer E et al., *Botulinum Toxin Type B: Experimental and Clinical Experience*, being chapter 6, pp. 71–85 of "Therapy With Botulinum Toxin", edited by Jankovic, J. et al. (1994) New York Marcel Dekker.

Nowinski W.L. et al., *Computer–Aided Stereotactic Functional Neurosurgery Enhanced by the Use of the Multiple Brain Atlas Database*, IEEE Trans Med Imaging 19(1);62–69:2000.

Oakman, S.A. et al., *Characterization of the Extent of Pontomesencephalic Cholinergic Neurons' projections to the Thalamus: Comparison with Projections to Midbrain Dopaminergic Groups*, Neurosci 94(2);529–547;1999.

Pearce, L.B., *Pharmacologic Characterization of Botulinum Toxin For Basic Science and Medicine*, Toxicon 35(9);1373–1412 at 1393.

Perry, et al., *Acetylcholine in Mind: a Neurotransmitter Correlate of Consciousness?*, TINS 22(6);273–280:1999.

R. Hagenah, *Effects of Type A Botulinum Toxin on the Cholinergic Transmission at Spinal Renshaw Cells and on the Inhibitory Interneurones*, Weigand et al, Nauny–Schmiedeberg's Arch. Pharmacol, 1976; 292, 161–165.

Richardson SB, et al., *Acetylcholine, Melatonin, and Potassium Depolarization Stimulate Release of Luteinizing Hormone–Releasing Hormone From Rat Hypothalamus In Vitro*, Proc Natl Acad Aci U.S.A. 79 (8): 2686–9,1982.

Rico, B. et al., *A Population of Cholinergic Neurons is Present in the Macaque Monkey Thalamus*, Eur J Neurosci, 10;2346–2352:1998.

Sanchez–Prieto, J., et al., *Botulinum Toxin A Blocks Glutamate Exocytosis From Guinea Pig Cerebral Cortical Synaptosomes*, Eur J. Biochem 165;675–681:1897.

Schafer M. K.–H. et al., *Cholinergic Neurons and Terminal Fields Revealed by Immunochemistry for the Vesicular Acetylcholine Transporter. I. Central Nervous System*, Neuroscience, 84(2);331–359:1998.

Scharfen. C.O., et al., *High Activity Iodine–125 Interstitial Implant For Gliomas*, Int. J. Radiation Oncology Biol Phys 24(4);583–591:1992.

Schuurman P.R., et al., *A Comparison of Continuous Thalamic Stimulation and Thalamotomy for Suppression of Severe Tremor*, NEJM 342(7);461–468:2000.

Shantz, E.J., et al, *Properties and Use of Botulinum Toxin and Other Microbial Neurotoxins in Medicine*, Microbiol Rev. 56;80–99:1992.

Singh, *Critical Aspects of Bacterial Protein Toxins*, pp. 63–84 (chapter 4) of Natural Toxins II, edited by B.R. Singh et al., Plenum Press, New York (1976).

Steriade M. et al., *Brain Cholinergic Systems*, Oxford University Press (1990), chapter 1 (pp. 3–62.

Stone T.W., *CNS Neurotransmitters and Neuromodulators: Acetylcholine*, CRC Press (1995), p. 16.

Tasker R., *Surgical Treatment of the Dystonias*, chapter 105, pp. 1015–1032, in Gildenberg P.L. et al., *Textbook of Stereotactic and Functional Neurosurgery*, McGraw–Hill (1998).

Tracey, D.J., et al., *Neurotransmitters in the Human Brain*, Plenum Press (1995), pp. 136–139.

Welch, J. et. al. *Stereotactic Radiosurgery for Cushings Disease and Prolactinoma*, Journal of Radiosurgery vol. 2, No. 1, pp. 23–29, 1999.

Sharma, Rewati R., et al.; *Minimally Invasive Neurosurgery Using CRW–3 Stereotaxy; Annals of Saudi Medicine*, 1994, vol. 14, No. 6, pp. 507–510.

Simonovic, I., et al.; *Acetylcholine and the Release of the Follicle–Stimulating Hormone–Releasing Factor; Endo*, 1974, vol. 95, No. 5, pp. 1373–1379.

Garzon, J. et al., *Effect of Intrathecal Injection of Pertussis Toxin on substance P, Norepinephrine and Serotonin Contents in Various Neural Structures of Arthritic Rats*, Life Sciences, vol. 47, pp. 1915–1923 XP–001011386.

* cited by examiner

METHOD FOR TREATING ENDOCRINE DISORDERS

BACKGROUND

The present invention relates to methods for treating endocrine disorders. In particular, the present invention relates to methods for treating endocrine disorders by intracranial administration of a neurotoxin.

The pituitary gland (the hypophysis) is a relatively small weighing only about 600 mg. The pituitary can be divided into an anterior lobe (the adenohypohysis) and a posterior lobe (the neurohypophysis). The functions of both lobes of the pituitary are heavily influenced by vascular and/or neural connections with the hypothalamus. The anterior pituitary makes six major hormones and stores two others. These are growth hormone (GH) which regulates growth and has important functions on intermediary metabolism; prolactin (PRL) which is necessary for lactation and which can suppress menstruation; luteinizing hormone (LH) and follicle stimulating hormone (FSH) both of which influence gonadal activity in men and women; thyroid stimulating hormone (TSH) which regulates thyroid function, and; adrenocorticotropin (corticotropin (ACTH) which controls glucocorticoid function of the adrenal cortex. Vasopresin (AVP, also called antidiuretic hormone, ADH) and oxytocin are produced in neurons of the hypothalamus and stored in the posterior lobe of the pituitary. AVP controls water conservation by the kidneys, while oxytocin is necessary for milk let-down during lactation and may aid in parturition.

The hypothalamus weighs about 4 grams and is the ventral and medial region of the diencephalon forming the walls of the ventral half of the third ventricle. It is delineated from the thalamus by the hypothalamic sulcus (a shallow groove between the dentate gyrus and the parahippocsmpal gyrus), lying medial to the internal capsule and subthalamus, continuous with the precommissural septum anteriorly and with the mesencephalic tegmentum and central gray substance posteriorly. The ventral surface of the hypothalamus can be identified by, proceeding from front to back along the ventral surface of the hypothalamus, the optic chiasma the unpaired infundibulum which extends by way of the infundibular stalk into the posterior lobe of the hypophysis and the paired mamillary bodies. Hypothalamus neurons have been grouped into various nuclei on the basis of functional characteristics. These hypothalamic nuclei include the supraoptic paraventricular, lateral preoptic, lateral hypothalamic, tuberal, anterior hypothalamic, ventmmedial, dorsomedial, arcuate, posterior hypothalamic, and premamillary nuclei and the mamilliary body.

The hypothalamus has afferent nerve fiber connections with the mesencephalon, limbic system, cerebellum and efferent fiber connections with the same structures and with the posterior lobe of hypophysis. Functional connection of the hypothalamus with the anterior lobe of the hypophysis is established by the hypothalmohypophysial portal system. The hypothalamus is prominently involved In the functions of the autonomic nervous system and, through its vascular link with the anterior lobe of the hypophysis, in endocrine mechanisms. The hypothalamus may also play a role in neural mechanisms underlying moods and motivational states. With regard to the endocrine hypothalamus, it is known that the arcuate nucleus of the hypothalamus is the major site of gonadotropin hormone releasing hormone (GnRH) production.

A single hypothalamic regulatory factor, GnRH, stimulates synthesis and secretion from the anterior pituitary of both FSH and LH in males and females. FSH and LH are collectively referred to as the gonadotropins. Other hypothalamic regulatory factors stimulate pituitary secretion of ACTH, TSH and GH, but inhibit the release of PRL from the anterior pituitary.

Vascular connection of the hypothalamus to the hypophysis is established when the neurosecretory neurons of the hypothalamus release regulatory (releasing and inhibiting) factors which reach the adenohypophysis through the portal circulation of the capillary plexus located in the median eminence region of the hypothalamus. These neurohemoral hypothalamic regulatory factors are small peptide neurohormones which, by influencing the secretion of adenohypophysial hormones, serve as the main functional link between the brain and the adenohypohysis. The hypothalamus is itself influenced by higher brain regions which employ various neurotransmitters, including dopamine, norepinephine, serotonin and acetylcholine to act upon the hypothalamus.

Addition of acetylcholine to anterior pituitary tissue incubated with hypothalamic fragments can result in the release of LH by the pituitary tissue and this LH release can be blocked by atropine (a muscarinic acetylcholine receptor (post synaptic) antagonist). Prostigmine, an acetylcholinesterase inhibitor, can also stimulate LH release in this system. Fiorindo R. P. et al., *Evidence for a Cholinergic Component in the Neuroendocrine Control of Luteinizing Hormone Secretion,* Neuroendocrinology 18: 322–332,1975.

Additionally, while as expected, FSH levels Increased upon addition of hypothalamic fragments to incubated anterior pituitary tissue, a further increase of pituitary FSH release is produced by acetylcholine. This enhanced FSH release is antagonized by atropine. Simonovic I, et al., *Acetylcholine and the Release of Follicle Stimulating Hormone Releasing Factor*, Endocrinology 95: 1371,1974.

Furthermore, cholinergic agents can stimulate release of gonadotropin-releasing hormone (GnRH) from the hypothalamus, which is blocked by atropine. GNRH acts in turn upon the anterior pituitary to promote the release of LH and FSH. Richardson S B, et al., *Acetylcholine, Melatonin, and Potassium Depoladzation Stimulate Release of Luteinizing Hormone-Releasing Hormone From Rat Hypothalamus in Vitro*, Proc Natl Acad Aci U.S.A. 79 (8): 268–9,1982. In intact rats, injection of acetylcholine into the lateral ventricle stimulates LH release. This can be blocked with atropine or enhanced with prostigmine.

Notably, hemicastration (removal of one ovary) in the female rat normally results in gonadotropin-mediated hypertrophy of the remaining ovary and this effect be blocked by atropine implants into the anterior hypothalamus. Monti J. M. et al., *Inhibition of Ovarian Compensatory Hypertophy by Implants of Atropine in the Hypothalamus*, Eperientia 26: 1263–1264,1970. Similar implants also blocked the post-orchidectomy rise in LH and FSH in male rats. Libertun C. et al., *Blockade of the Postorchidectomy Increase in Gonadotropin by Implants of Atropine into the Hypothalamus*, Proc Soc Exp Biol Med 152: 143–146,1976. These data are consistent with the existence of a muscarinic cholinergic mechanism mediating GnRH release in the hypothalamus, clearly indicating therefore a stimulatory cholinergic influence over hypothalamic activity.

Additional studies have indicated that the net effect of acetylcholinesterase inhibition or acetylcholine administration to the hypothalamus stimulates gonadotropin secretion. See e.g. Blake C A., *Parallelism and Divergence in Luteinizing and Follicle Stimulating Hormone Release in Nicotine-*

*Treated Rats*, Proc Soc Exp Biol Med 145: 716–720, 1974; Kanematsu S. et al., *Inhibition of the Progesterone-Advanced LH Surge at Proestrus*, Proc Soc Exp Biol Med 143: 1183–5,1973; Blake C. A., et al., *Nicotine Delays the Ovulatory Surge of Luteinizing Hormone in the Rat*, Proc Soc Exp Biol Med 141: 1014–1016,1972; Blake C. A. et al., *Localization of the Inhibitory Actions of Estrogen and Nicotine on Release of Luteinizing Hormone in Rats*, Neuroendocrinology 16: 22–35,1974, and; Blake C. A. et al., *Effects of Hypothalamic Deafferentation and Ovarian Steroids on Pituitary Responsiveness to LH-RH in Female Rats*. In Gual and Rosemberg, eds, *Hypothalamic Hypophysiotropic Hormones*. Excerpta Medica, Amsterdam, 1973, pp. 33–38.

With few exceptions (testosterone in men, progesterone in men and women) hormone excess causes pathological effects. Thus, excessive secretion of growth hormone or GHRH causes acromegaly in adults or gigantism in adolescents, if the excessive secretion starts before epiphyseal closure. With regard to prolactin, pathological hyperprolactinemia is a common cause of infertility in women, since elevated prolactin level results in suppression of a normal menstrual cycle. The primary physiological effect of the gonadotropins is the promotion of gametogenesis and/or gonadal steroid production. In the male, LH stimulates production of testosterone. Testosterone is required for sperm production, maintenance of sexual libido and secondary sexual characteristics. FSH is required for normal sperm production. In the female, the overall effect of FSH is to promote the growth of the developing follicle, whereas the overall effect of LH is to induce ovulation.

Current therapies for endocrine hypothalamic and pituitary disorders have significant drawbacks and deficiencies. Treatment for endocrine disorders primary to pituitary hyperplasia include medical (drug) therapy. Thus, prolactin-secreting pituitary adenoma (prolactinoma) has been treated with systemically administered bromocriptine or other dopamine agonists. Unfortunately, tumor activity typically returns when drugs are withdrawn. When medical therapy is unsuccessful, surgical resection, by transphenoidal surgery, is a standard procedure. The pituitary gland can be surgically approached by the transphenoidal (through the sphenoid sinus to the pituitary fossa), transethmoidal (through an incision in the medial orbital wall), transoral and transfrontal (craniotomy) routes. See e.g. Lindsay K. W. et al., *Neurology and Neurosurgery Illustrated*, pages 303 and 332, Churchill Livingstone, third edition (1997). Surgical intervention carries the risk of incurring a dysfunction induced by the surgery itself, such as hypopituitarism (including diabetes insipidus) and visual loss, as well as mortality.

Radiosurgery, including stereotactic radiosurgery has been used to treat various hyperplasic and hypertrophic pituitary disorders, including pituitary neoplasms. See e.g. Williams, J. et. al. *Stereotactic Radiosurgery for Cushings Disease and Prolactinoma*, Journal of Radiosurgery Vol. 2, No. 1, pages 23–29, 1999. Radiation therapy carries the risk of hypopituitarism and radiation Injury to the brain and optic apparatus.

The human hypothalamus was practically surgically inaccessible until the advent of stereotactic surgery and the earliest reported stereotactic surgery performed upon a human hypothalamus was by Speigel and Wyeis in 1949. Stereotactic neurosurgery has been practised for therapeutic hypothalamotomy through use of chronic electrical stimulation or permanent ablative lesioning for effective palliation of functional aberrations of the hypothalamus to treat various indications, including erethistic hyperkinesis, intractable pain, addiction (alcohol and drug) and sexual hyperkinesis. See e.g. Sharma, R. R., et al., *Minimally Invasive Neurosurgery Using CRW-3 Stereotaxy*, Ann Saudi Med 1994;14 (6):507–510. Hypothalamic stereotactic target coordinates have included from 1 mm anterior to the midpoint of the intercommisural line to 2 mm posterior to the midpoint, 2 to 4 mm below the intercommisural line, and 2 mm lateral to the lateral wall of the third ventricle. Notably, stereotactic therapeutic lesioning hypothalamotomy has been carried out by injecting wax through a stereotatically inserted needle. Hunter, S., *Stereotactic Hypothalamotomy*, chapter 153, pages 1507–1517 of *Textbook of Stereotactic and Functional Neurosurgery*, edited by Gildenberg P. L. et al., McGraw-Hill (1998). A device useful for chronic intracranial delivery of a pharmaceutical is disclosed by PCT/US99/17880 (WO 00/07652).

Stereotactic techniques developed initially for lesion making, enable accurate placement of a cannula or electrode at a predetermined target site within the brain. Many different stereotactic frames have been developed, e.g. Leksell, Todd-Wells, Guiot. These combined with radiological landmarks (usually ventriculography or use of CT/MRI) and a brain atlas permit anatomical localization to within about one mm. Since some functional variability occurs at each anatomical site, localization can also based be upon recorded neuronal activity and the effects of electrical stimulation. Stereotactic surgery permits millimeter precision placement of a probe, electrode, catheter, or hollow needle at a desired intracranial location. It is also known to stereotatically implant a radioactive seed (such as yttrium$^{90}$) to cause deep brain tumor necrosis, as in craniopharyngioma and it is known to carry out stereotactic biopsy of various intracranial tumors, including hypothalamic astrocytoma. Additionally, thalamotomy and/or subthalamotomy or campotomy are known neurosurgical procedures for treating movement disorders, such as dystonia, through stereotactic surgery. Tasker R., *Surgical Treatment of the Dystonias*, chapter 105, pages 1015–1032, in Gildenberg P. L. et al., *Textbook of Stereotactic and Functional Neurosurgery*, McGraw-Hill (1998). A variety of techniques exist to permit precise guidance to location of a probe, including computed tomography and magnetic resonance imaging. Notably, hypothalamic ablation results in an irreversible destructive brain lesion.

Therapies such as deep brain electrode stimulation can create problems due to wire erosion, lead friction, infection of the implantable pulse generator, malfunction of the implantable pulse generator, electrical shock and lead migration. Other complications due to electrode stimulation can include dysarthria, disequilibrium, paresis and gait disorder. See e.g. Koller, W. C. et al., *Surgical Treatment of Parkinson's Disease*, J Neurol Sci 167;1–10:1999, and Schuurman P. R., et al., *A Comparison of Continuous Thalamic Stimulation and Thalamotomy for Suppression of Severe Tremor*, NEJM 342(7);461–468:2000.

Aside from surgical ablation or stimulation, external radiotherapy (gamma knife radiosurgery) has also been used for the treatment of a number of drug resistant maladies of intracranial origin. Drawbacks with this procedure are that a positive therapeutic result may not occur until up to eight months after the radiosurgery, and the long term benefits as well as radiation side effects are currently unknown.

Botulinum Toxin

The bacterial genus *Clostridium* includes more than one hundred and twenty seven species, grouped according to morphology and function. The anaerobic, gram positive bacterium *Clostridium botulinum* produces a potent polypeptide neurotoxin, botulinum toxin, which causes the neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating food infected with a *Clostridium botulinum* culture or spores. The botulinum toxin can apparently pass unattenuated through the lining of the gut and attack peripheral motor nerves. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1]Available from Allergan, Inc., of Irvine, Calif. under the tradename BOTOX® in 100 unit vials)

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71–85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of a motor neuron through a specific interaction between the heavy (or H) chain of the botulinum toxin and a neuronal cell surface receptor. The receptor is believed to be different for each type of botulinum toxin and for tetanus toxin. The carboxyl end segment of the H chain, $H_C$, appears to be important for targeting of the toxin to the surface of the motor neuron.

In the second step, the toxin crosses the plasma membrane of the motor neuron. The toxin is first engulfed by the cell through receptor-mediated endocytosis, and an endosome containing the toxin is formed. The toxin then escapes the endosome into the cytoplasm of the cell. This step may be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light (or L) chain of the toxin. The entire toxic activity of botulinum toxin and of the tetanus toxin is contained in the L chain of the holotoxin. The L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C cleaves syntaxin and SNAP-25. Each of the botulinum toxins specifically cleaves a different bond, except botulinum toxin type B and tetanus toxin which cleave the same bond.

Botulinum toxins have been used in clinical settings for the treatment of neuromuscular disorders characterized by hyperactive skeletal muscles. A botulinum toxin type A complex has been approved by the U.S. Food and Drug Administration for the treatment of blepharospasm, strabismus and hemifacial spasm. Non-type A botulinum toxin serotypes apparently has a lower potency and/or a shorter duration of activity as compared to botulinum toxin type A. Most if not all of the botulinum toxins can, upon intramuscular injection, produce significant muscle paralysis within one day of the injection, as measured, for example, by the mouse Digit Abduction Score (DAS). Aoki K. R., *Preclinical Update on BOTOX (Botulinum Toxin Type A)-Purified Neurotoxin Complex Relative to Other Botulinum Toxin Preparations*, Eur J. Neur 1999, 6 (suppl 4):S3-S10. Maximal clinical effect may not result for several days. The typical duration of symptomatic relief from a single intramuscular injection of botulinum toxin type A averages about three months. Apparently, a substrate for a botulinum toxin can be found in a variety of different cell types. See e.g. *Biochem*,J 1;339 (pt 1):159–65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant heurotoxin complex) may act to provide stability against denaturation to the botulinum toxin molecule and protection against digestive acids when toxin Is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium ation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522–527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675–681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9);1373–1412 at 1393; Bigalke H., et al., *Botulinum A Neurotoxin Inhibits Non-Cholinergic Synaptic Transmission in Mouse Spinal Cord Neurons in Culture*, Brain Research 360;318–324:1985; Habermann E., *Inhibition by Tetanus and Botulinum A Toxin of the release of [$^3$H]Noradrenaline and [$^3$H]GABA From Rat Brain Homogenate*, Experentia 44;224–226:1988, Bigalke H., et al., Tetanus Toxin and *Botulinum A Toxin Inhibit Release and Uptake of Various Transmitters, as Studied with Particulate Preparations From Rat Brain and Spinal Cord*, Naunyn-Schmiedeberg's Arch Pharmaol 316;244–251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geqq 3\times 10^7$ U/mg, an $A_{260}$ /$A_{278}$ of less than 0.60 and a distinct pattern of banding on gel electrophoresis. The known Shantz process can be used to obtain crystalline botulinum toxin type A, as set forth in Shantz, E. J., et al, *Properies and Use of Botulinum Toxin and Other Microbial Neurotoxins in Medicine*, Microbiol Rev. 56;80–99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1–2\times 10^8$ $LD_{50}$ U/mg or greater; purified botulinum toxin type B with an approximately 156 kD molecular weight with a specific potency of $1–2\times 10^8$ $LD_{50}$ U/mg or greater, and; purified botulinum toxin type F with an approximately 155 kD molecular weight with a specific potency of $1–2\times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down , U. K.; Wako (Osaka, Japan), Metabiologics (Madison, Wis.) as well as from Sigma Chemicals of St Louis, Mo.

Both pure botulinum toxin and botulinum toxin complexes can be used to prepare a pharmaceutical composition. Both pure botulinum toxin and botulinum toxin complexes, such a the toxin type A complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are Intracellular peptidases) is dependent, at least in part, upon their three dimensional conformation. Thus, botulinum toxin type A is detoxified by heat, various chemicals surface stretching and surface drying. Additionally, it Is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product Is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249–53:1997.

It has been reported that botulinum toxin type A has been used in clinical settings as follows:

(1) about 75–125 units of BOTOX® per intramuscular injection (multiple muscles) to treat cervical dystonia;

(2) 5–10 units of BOTOX® per intramuscular injectiori to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although R has been reported that results have not been impressive. Marjama-Jyons, J., et al., *Tremor-Predominant Parkinson's Disease*, Drugs & Aging 16(4); 273–278:2000.

It is known that botulinum toxin type A can have an efficacy for up to 12 months (*European J. Neurology* 6 (Supp 4): S111–S11150:1999), and in some circumstances for as long as 27 months. *The Laiyngoscope* 109:1344–1346:1999. However, the usual duration of an intramuscular injection of Botox® is typically about 3 to 4 months.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves.

Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. *Eur J Neurol* 1999 Nov;6(Suppl 4):S3-S10.

In addition to having pharmacologic actions at the peripheral location, botulinum toxins may also have inhibitory effects in the central nervous system. Work by Weigand et al, *Nauny-Schmiedeberg's Arch. Pharmacol.* 1976;292, 161–165, and Habermann, *Nauny-Schmiedeberg's Arch. Pharmacol.* 1974;281, 47–56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic.nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane Ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Cholineraic Brain Systems

Cholinergic influence of both the motor and visual thalamus originates from both the brainstem and the basal forebrain. See e.g. Billet S., et al., *Cholinergic Projections to the Visual Thalamus and Superior Colliculus*, Brain Res. 847;121–123:1999 and Oakman, S. A. et al., *Characterization of the Extent of Pontomesencephalic Choinergic Neurons' projections to the Thalamus: Comparison with Projections to Midbrain Dopaminergic Groups*, Neurosci 94(2); 529–547;1999. Thus, it is known based on histochemical studies using acetylcholinesterase (AchE) staining and retrograde tracing with choline acetyltransferase (ChAT) immunochemistry that there can be ascending cholinergic stimulation by the brainstem of thalamic neurons. Steriade M. et al., *Brain Cholinergic Systems*, Oxford University Press (1990), chapter 1. Indeed, many thalamic nuclei receive dense cholinergic innervation from brainstem reticular formations. Ibid, page 167. Known brainstem cholinergic cell groups are located within: (1) the rostral pons at what is termed a Ch5 location, which is located within the central tegmental field around the brachium conjunctivum, forming a pedunculopontine tegmental nucleus, and; (2) the caudal part of the midbrain, at what is termed a Ch6 location, the laterodorsal tegmental nucleus, which is embedded in the periaqueductal and periventricular gray matter. The Ch5 and Ch6 cell groups can consist almost exclusively of cholinergic neurons and together form the pontine cholinergic system. The Ch5 Ch6 cholinergic groups provide direct ascending projections that terminate in a number of target structure in the midbrain, diencephalon and telencephalon, including the superior colliculus, anterior pretectal area, interstitial magnocellular nucleus of the posterior commissure, lateral habenular nucleus, thalamus, magnocellular preoptic nucleus, lateral mammillary nucleus, basal forebrain, olfactory bulb, medial prefrontal cortex and pontine nuclei. Stone T. W., CNS *Neurotransmitters and Neuromodulators: Acetylcholine*, CRC Press (19950, page 16. See also Schafer M. K.-H. et al., *Cholinergic Neurons and Terminal Fields Revealed by Immunochemistry for the Vesicular Acetylcholine Transporter*. L Central Nervous System, Neuroscience, 84(2);331–359:1998. Three dimensional localization of Ch1–8 cholinergic nuclei have been mapped in humans. See e.g. Tracey, D. J., et al., *Neurotransmitters in the Human Brain*, Plenum Press (1 i995), pages 13–6139.

Additionally, the basal forebrain (proencephalon) provides cholinergic Innervation of the dorsal thalamus, as well as to the neocortex, hippocampus, amygdala and olfactory bulb. See e.g. Steridae, page 136–136. Basal forebrain areas where the great proportion of neurons are cholinergic include the medial septal nucleus (Ch1), the vertical branches of the diagonal band nuclei (Ch2), the horizontal branches of the diagonal band nuclei (Ch3), and the magnocellular nucleus basalis (Ch4), which is located dorsolaterally to the Ch3 cell group. Ch1 and Ch2 provide the major component of cholinergic projection to the hippocampus. The cells in the Ch3 sector project to the olfactory bulb.

Furthermore, cholinergic neurons are present in the thalamus. Rico, B. et al., *A Population of Cholinergic Neurons is Present in the Macaque Monkey Thalamus*, Eur J Neurosci, 10;2346–2352:1998.

Abnormalities in the brain's cholinergic system have been consistently identified in a variety of neuropsychiatric disorders including Alzheimer's disease, Parkinson's disease and dementia with Lewy bodies. Thus, in Alzheimer's disease there Is hypoactivity of cholinergic projections to the hippocampus and cortex. In individuals with dementia with Lewy bodies extensive neocortical cholinergic deficits are believed to exist and in Parkinson's disease there is a loss of pedunculopontine cholinergic neurons. Notably, in vivo imaging of cholinergic activity in the human brain has been reported. Perry, et al., *Acetylcholine in Mind: a Neurotransmitter Correlate of Consciousness*?, TINS 22(6); 273–280:1999.

What is needed therefore is a method for effectively treating an endocrine disorder by administration of a pharmaceutical which has the characteristics of long duration of activity, low rates of diffusion out of a chosen intracranial target tissue where administered, and nominal systemic effects at therapeutic dose levels.

SUMMARY

The present invention meets this need and provides methods for effectively treating a variety of endocrine disorders by intracranial administration of a neurotoxin which has the characteristics of long duration of activity, low rates of diffusion out of an intracranial site where administered and insignificant systemic effects at therapeutic dose levels.

The following definitions apply herein:

"About" means approximately or nearly and In the context of a numerical value or range set forth herein means ±10% of the numerical value or range recited or claimed.

"Biological activity" includes, with regard to a neurotoxin, the ability to influence synthesis, exocytosis, receptor binding and/or uptake of a neurotransmitter, such as acetylcholine, or of an neuroendocrine secretory product, such as a hypothalamic regulatory factor.

"Botulinum toxin" includes pure botulinum toxin (i.e. the approximately 150 kD toxin molecule) and botulinum toxin complexes (i.e. the pure botulinum toxin molecule in association with non-toxin molecules, such as haemagglutins, to form a complex of up to about 900 kD).

"Local administration" means direct administration of a pharmaceutical at or to the vicinity of a site on or within an animal body, at which site a biological effect of the pharmaceutical is desired. Local administration excludes systemic routes of administration, such as intravenous or oral administration.

"Neurotoxin" means a biologically active molecule with a specific affinity for a neuronal cell surface receptor. Neurotoxin includes Clostridial toxins both as pure toxin and as complexed with one to more non-toxin, toxin associated proteins "Intracranial" means within the cranium or at or near the dorsal end of the spinal cord and includes the medulla, brain stem, pons, cerebellum and cerebrum. The hypophysis and the hypothalamus are both considered to be intracranial.

A method for treating an endocrine disorder according to the present invention can comprise the step of intracranial administration of a neurotoxin to a patient, thereby alleviating a symptom of an endocrine disorder. The neurotoxin can be made, for example, by a bacterium selected from the group consisting of *Clostridium botulinum, Clostridium butyricum, Clostridium beratt*, and *Clostridium tetani* or can be expressed by a suitable host (i.e. a recombinantly altered *E. coli*) which encodes for a neurotoxin made non-recombinantly by a *Clostridium botulinum, Clostidium butyricum, Clostridium beratti* or *Clostridium tetani*. Preferably, the neurotoxin is a botulinum toxin, such as a botulinum toxin type A, B, $C_1$, D, E, F and G. More preferably, the botulinum toxin is botulinum toxin type A because of the high potency, ready availability and long history of clinical use of botulinum toxin type A to treat various disorders.

The botulinum toxin can be locally administered in an amount of between about 102 units and about 500 units and the endocrine disorder symptom alleviating effect from a local administration of a botulinum toxin according to the present invention can persist for between about 1 month and about 5 years.

Notably, the neurotoxin can be administered to the hypothalamus, such as to the median eminence region and/or arcuate nucleus area of the hypothalamus. Additionally, the neurotoxin can be administered to the pituitary gland, including to the anterior pituitary or posterior pituitary. The intracranial administration step can comprise the step of implantation of a controlled release botulinum toxin implant.

A detailed embodiment of a method within the scope of the present invention for treating an endocrine disorder can comprise the step of intracranial administration of a therapeutically effective amount of a botulinum toxin to a patient, thereby treating a symptom of an endocrine disorder. The endocrine disorders treatable by a method according to the present invention include afflictions which result from an excess of any of the hypothalamic releasing factors or of any of the pituitary hormones, including GnRH, GH, LH and/or FSH. Thus endocrine disorders such as, for example, acromegaly, gigantism, Cushings disease, hypergonadism and hyperthyroidism, can be treated by a method according to the present invention.

A further detailed embodiment of a method within the scope of the present invention for treating an endocrine disorder can comprise the steps of: selecting a neurotoxin (such as a botulinum toxin)with hypothalamic releasing hormone, or pituitary hormone, suppressant activity: choosing a hypothalamic or pituitary target tissue which influences an endocrine disorder; and; intracranially administering to the target tissue a therapeutically effective amount of the neurotoxin selected, thereby treating the endocrine disorder.

A method for treating hypergonadism according to the present. invention can comprise the step of in vivo local administration of a therapeutically effective amount of a botulinum toxin type A to a cholinergically influenced hypothalamic tissue to a human patient, thereby alleviating a symptom of hypergonadism in the patient.

Additionally, a contraceptive method according to the present invention can comprise the step of intracranial administration of a botulinum toxin (such as a botulinum toxin type A) to a patient, thereby reducing an intracranial secretion of a hormone required for gametogenesis. Thus, ovulation can be inhibited by intracranial administration of a botulinum toxin to a patient, thereby reducing an intracranial secretion of a hormone which influences ovulation. Furthermore, sperm production can be inhibited by intracranial administration of a botulinum toxin to a patient, thereby reducing an intracranial secretion of a hormone which influences production.

The neurotoxin can be a modified neurotoxin, that is a neurotoxin which has at least one of its amino acids deleted, modified or replaced, as compared to a native or the modified neurotoxin can be a recombinant produced neurotoxin or a derivative or I have surprising found that a botulinum toxin, such as botulinum toxin type A, can be intracranially administered in amounts between about $10^{-2}$ units to about 500 units to alleviate an endocrine disorder experienced by a human patient. Preferably, the botulinum toxin used is intracranially administered in an amount of between about $10^{-1}$ unit and about 50 units. More preferably, the botulinum toxin is administered in an amount of between about $10^{-1}$ units and about 5 units. Most preferably, from about 0.01 units to about 10 units of a botulinum toxin type A and from about 0.1 to about 100 units of a botulinum toxin type B is used is a method practiced according to the present disclosed invention. With regard to the other botulinum toxin serotypes (including toxin types E and F) the unit dosage to be used is within the range of about 0.01 units to about 500 units, as set forth herein. Significantly, the endocrine disorder alleviating effect of the present disclosed methods can persist for between about 2 months to about 6 months when administration is of aqueous solution of the neurotoxin, and for up to about five years when the neurotoxin is administered as a controlled release implant.

Another preferred method within the scope of the present invention is a method for improving patient function, the method comprising the step of intracranially administering a neurotoxin to a patient, thereby improving patient function as determined by improvement in one or more of the factors of reduced pain, reduced time spent in bed, increased ambulation, healthier attitude and a more varied lifestyle.

DESCRIPTION

The present invention is based on the discovery that one or more endocrine disorders can be effectively treated by intracranial, in vivo, local administration of an neurotoxin to a human patient. Generally, hormonal excess results in a pathological condition and one aspect of the present invention is directed to methods for treating hormone excess resulting from overproduction of a hypothalamic releasing factor or of a pituitary hormone. The present invention is also based on the discovery that gametogenesis, and hence conception, can be inhibited by intracranial, in vivo, local administration of an neurotoxin to a male or female human patient.

Thus, the present invention reveals that significant and lost lasting relief from a variety of different endocrine disorders can be achieved by intracranial administration of a neurotoxin. Intracranial administration permits the blood brain barrier to be bypassed and delivers much more toxin to the brain than is possible by a systemic route of administration. Furthermore, systemic administration of a neurotoxin, such as a botulinum toxin, is contraindicated due to the severe complications (i.e. botulism) which can result from entry of a botulinum toxin into the general circulation. Additionally, since botulinum toxin does not penetrate the blood brain barrier to any significant extent, systemic administration of a botulinum toxin has no practical application to treat an intracranial target tissue.

According to the present, in vivo local administration of a neurotoxin, such as a botulinum toxin, can be used to treat a variety of conditions which can benefit from inhibition of the hypothalamic-pituitary-gonadal axis such as hypergonadotrophic hypergonadism. Thus, a method according to the present invention can be used to treat hypergonadotrophic hypergonadism by decreasing a hypothalamic or pituitary secretion.

Additionally, a method according to the present can be used to influence the secretion of gonadotropin releasing hormone (GnRH) by locally administering a preparation influencing central cholinergic activity. In brief, the present invention provides methods for treatment of conditions that can benefit from inhibition of the hypothalamic-pituitary-gonadal axis, for prevention gametogenesis (i.e. inhibition of ovulation or of sperm production—hence contraception) and to treat hypergonadotrophic hypergonadism.

Without wishing to be bound by theory it can be hypothesized that a mechanism by which a method according to the present invention achieves a desired result is due to inhibition of a cholinergic influence over an endocrine hypothalamic or pituitary tissue by the disclosed local administration of a neurotoxin. Inhibition of a hypothalamic cholinergic influence results, for example, in a decreased release of hypothalamic GnRH, which in turn causes a reduced anterior pituitary release of LH and FSH. A reduction is circulating LH and FSH release can be an effective means of inhibiting conception, and treating various hypergonadic conditions. Thus, a neurotoxin, such as a botulinum toxin, can inhibit neuronal exocytosis of several different CNS neurotransmitters, in particular acetylcholine. It is known that cholinergic neurons are present in both the hypothalamus and in the pituitary. Thus, target tissues for a method within the scope of the present invention can include neurotoxin induced reversible denervation of intracranial areas, such as the hypothalamus. For example, injection or implantation of a neurotoxin to a cholinergically innervated hypothalamic nuclei (such as the arcuate nucleus) can result in a suppression of GHRH and thus GH secretion due to the action of the toxin upon cholinergic terminals projecting into the hypothalamus, and; (2) attenuation of hypothalamic regulatory hormone output due to the action of the toxin upon hypothalamic somata, both cholinergic and non-cholinergic, thereby producing a chemical and therapeutic hypothalamotomy.

As disclosed, the present invention relates to use of a neurotoxin to modulate the hypothalamic-pituitary-gonadal axis through a direct, local administration of a neurotoxin to the hypothalamus and or to the pituitary. In particular, the present invention relates to local, central administration of a neurotoxin to modulate the hypothalamic-pituitary-gonadal axis by inhibiting the secretion of gonadotropin releasing hormone (GnRH) from the hypothalamus.

Suitable neurotoxins for use in the present invention include non-cytotoxic (i.e. no significant neuron or other cell death/necrosis) neurotoxins which can reversibly inhibit one or hypothalamic and/or pituitary endocrine secretions without significant effect, upon other non-hypothalamic or non-pituitary target tissue. Suitable compounds for this purpose are the botulinum toxins.

The present invention encompasses any suitable method for intracranial administration of a neurotoxin to a selected target tissue, including injection of an aqueous solution of a neurotoxin and implantation of a controlled release system, such as a neurotoxin incorporating polymeric implant at the selected target site. Use of a controlled release implant reduces the need for repeat injections. Intracranial implants are known. For example, brachytherapy for malignant gliomas can include stereotatically implanted, temporary, iodine-125 interstitial catheters. Scharfen. C. O., et al., *High Activity Iodine-125 Intersitial Implant For Gliomas*, Int. J. Radiation Oncology Biol Phys 24(4);583–591:1992. Additionally, permanent, intracranial, low dose $^{125}$I seeded catheter implants have been used to treat brain tumors. Gaspar, et al., *Permanent $^{125}$I Implants for Recurrent Malignant Gliomas*, Int J Radiation Oncology Biol Phys 43(5); 977–982:1999. See also chapter 66, pages 577–580, Bellezza D., et al., *Stereotactic Interstitial Brachytherapy*, in Gildenberg P. L. et al., *Textbook of Stereotactic and Functional Neurosurgery*, McGraw-Hill (1998).

Furthermore, local administration of an anti cancer drug to treat malignant gliomas by interstitial chemotherapy using surgically implanted, biodegradable implants is known. For example, intracranial administration of 3-bis(chloro-ethyl)-1-nitrosourea (BCNU) (Carmustine) containing polyanhydride waters, has found therapeutic application. Brem, H. et al., *The Safety of Interstitial Chemotherapy with BCNU-Loaded Polymer Followed by Radiation Therapy in the Treatment of Newly Diagnosed Malignant Gliomas: Phase I Trial*, J Neuro-Oncology 26:111–123:1995.

A polyanhydride polymer, Gliadel® (Stolle R & D, Inc., Cincinnati, OH) a copolymer of poly-carboxyphenoxypropane and sebacic acid in a ratio of 20:80 has been used to make implants, intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2–3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gilomas*, Lancet 345;10081012:1995.

An implant can be prepared by mixing a desired amount of a stabilized neurotoxin (such as non-reconstituted BOTOX®) into a solution of a suitable polymer dissolved in methylene chloride, at room temperature. The solution can then transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672–684:1998. Diffusion of biological activity of a botulinum toxin within a tissue appears to be a function of dose and can be graduated. Jankovic J., et al *Therapy With Botulinum Toxin*, Marcel Dekker, Inc., (1994), page 150.

Local, intracranial delivery of a neurotoxin, such as a botulinum toxin, can provide a high, local therapeutic level of the toxin and can significantly prevent the occurrence of any systemic toxicity since many neurotoxins, such as the bolulinum toxins are too large to cross the blood brain barrier. A controlled release polymer capable of long term, local delivery of a neurotoxin to an intracranial site can circumvent the restrictions imposed by systemic toxicity and the blood brain barrer, and permit effective dosing of an intracranial target tissue. Suitable neurotoxin and botulinum toxin implants for use In the present invention, are set forth in co-pending U.S. patent applications Ser. No. 09/587250 entitled “Neurotoxin Implant and Ser. No. 09/624003, entitled “Botulinum Toxin Implant”. Such an implant permits direct introduction of a chemotherapeutic agent to a brain target tissue via a controlled release polymer. The implant polymers used are preferably hydrophobic so as to protect the polymer incorporated neurotoxin from water induced decomposition until the toxin is released into the target tissue environment.

Local intracranial administration of a botulinum toxin, according to the present invention, by injection or implant to e.g. the cholinergic hypothalamus presents as a superior alternative to hypothalamotomy in the management of inter alia hypergonadothophism.

A method within the scope of the present invention includes stereotactic placement of a neurotoxin containing implant using the Riechert-Mundinger unit and the Z D (Zamorano-Dujovny) multipurpose localizing unit. A contrast-enhanced computerized tomography (CT) scan, injecting 120 ml of omnipaque, 350 mg iodine/ml, with 2 mm slice thickness can allow three dimensional multiplanar treatment planning (STP, Fischer, Freiburg, Germany). This equipment permits planning on the basis of magnetic resonance imaging studies, merging the CT and MRI target information for clear target confirmation.

The LekseII stereotactic system (Downs Surgical, Inc., Decatur, Ga.) modified for use with a GE CT scanner (General Electric Company, Milwaukee, Wis.) as well as the Brown-Roberts-Wells (B R W) stereotactic system (Radionics, Burlington, Md.) have been used for this purpose. Thus, on the morning of the implant, the annular base ring of the B R W stereotactic frame can be attached to the patient’s skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and B R W space.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection. Botulinum toxin type B is a less preferred neurotoxin to use in the practice of the disclosed methods because type B is known to have a significantly lower potency and efficacy as compared, to type A, is not readily available, and has a limited history of clinical use in humans. Furthermore, the higher protein load with regard to type B can cause immunogenic reaction to occur with development of antibodies to the type B neurotoxin.

The amount of a neurotoxin selected for intracranial administration to a target tissue according to the present disclosed invention can be varied based upon criteria such as the endocrine disorder being treated, its severity, the extent of brain tissue involvement or to be treated, solubility characteristics of the neurotoxin toxin chosen as well as the age, sex, weight and health of the patient. For example, the extent of the area of brain tissue influenced is believed to be proportional to the volume of neurotoxin injected, while the quantity of the hypothalamic or pituitary secretion suppressant effect is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill).

I have found that a neurotoxin, such as a botulinum toxin, can be intracranially administered according to the present disclosed methods in amounts of between about $10^{-2}$ units to about 500 units. A dose of about $10^{-2}$ units can result in a gonadotrophin suppressant effect if delivered a small nuclei. Intracranial administration of less than about $10^{2}$ units does not result in a significant or lasting therapeutic result. An intracranial dose of more than 500 units of a neurotoxin, such as a botulinum toxin, poses a significant risk of denervation of sensory or desirable motor functions of neurons adjacent to the target Less than about $10^{-2}$ U/kg can result in a relatively minor, though still observable, gonadotrophin suppressant effect. A more preferred range for intracranial administration of a botulinum toxin, such as botulinum toxin type A, so as to achieve a gonadotrophin suppressant effect in the patient treated is from about $10^{-1}$ U/kg to about 50 units. Less than about $10^{-1}$ U/kg can result in the desired therapeutic effect being of less than the optimal or longest possible duration. A most preferred range for intracranial administration of a botulinum toxin, such as botulinum toxin type A, so as to achieve a desired gonadotrophin suppressant effect in the patient treated is from about 0.1 units to about 10 units. Intracranial administration of a botulinum toxin, such as botulinum toxin type A, in this preferred range can provide dramatic therapeutic success.

The present invention includes within its scope the use of any neurotoxin which has a long duration gonadotrophin suppressant effect when locally applied intracranially to the patient. For example, neurotoxins made by any of the species of the toxin producing *Clostridium* bacteria, such as *Clostridium botulinum, Clostridium butydricum*, and *Clostridium beratti* can be used or adapted for use in the methods of the present invention. Additionally, all of the botulinum serotypes A, B, $C_1$, D, E, F and G can be advantageously used in the practice of the present invention, although type A is the most preferred and type B the least preferred serotype, as explained above. Practice of the present invention can provide a gonadotrophin suppressant effect, per injection, for 3 months or longer in humans.

SignifIcantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function Is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting treatment of an endocrine disorder can be achieved by intracranial administration of a neurotoxin to an afflicted patient. In its most preferred embodiment, the present invention is practiced by intracranial injection or implantation of botulinum toxin type A.

The present invention does include within its scope: (a) neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water.

EXAMPLES

The following examples set forth specific methods encompassed by the present invention to treat an endocrine disorder or to inhibit contraception and are not intended to limit the scope of the invention.

A preferred method for local administration of a neurotoxin to a pituitary target tissue according to the present invention is the transphenoidal approach. This surgical approached to the pituitary is carried out by, after preping the patient, including steroid cover, making an incision in the upper gum. The nasal mucosa is stripped from the septum and the pituitary fossa approached through the sphenoid sinus.

For a stereotactic approach (i.e. to the endocrine hypothalamus), a suitable stereotaxis needle (2"–6" long, stiff, hollow bore, non-coring, with an outside diameter of less than one millimeter, for recordation, stimulation and administration of a neurotoxin, such as a botulinum toxin) can be obtained from Popper & Sons (New Hyde Park, N.Y.) or from Surgical911.Com (Old Saybrook, Conn.). A preferred stereotactic needle is 32 guage (32G, 0.009"/0.229 mm O.D.) (Popper & Sons). With stereotaxis, endotracheal general anesthesia is followed by making a frontal burr hole at the coronal suture. A fine catheter is used for ventriculography with air or a small amount of contract medium. Using the anterior and posterior commissures as landmarks, a fine needle, 0.8 mm diameter is stereotactically inserted into the target point located at, for example the arcuate nucleus using a CRW apparatus. Use of the Axon Clinical Micmpositioner (Axon, Instruments, Inc., Foster City, Calif.) in conjunction with either the Leksell-G or Radionics-CRW sterotaxis frame permits needle placement at or within 50 microns of a desired intracranial target site. Electroencephalography (EEG), electrocorticography (ECG) and electromyography (EMG) of the neck muscles, blood pressure and respiration are monitored. After confirming the proper placement of the needle into the target point by means of radiograph and stimulating studies, 0.5 units of a botulinum toxin type A (such as Botox) can be injected or an implant capable of releasing about 0.5 units of the botulinum toxin over a 3–4 month period for a continuos period of 2–5 years is implanted at the target tissue site. The desired treatment zone is 2–3 mm in diameter. The number of passes to target is limited to an absolute minimum.

Example 1

Intracranial Target Tissue Localization and Methodology

Sterootactic procedures can be used for precise intracranial administration of neurotoxin in aqueous form or as an implant to downregulate a hypertrophic endocrine hypothalamus or pituitary. Thus, intracranial administration of a neurotoxin to treat an endocrine can be carried out as follows.

A preliminary MRI scan of the patient can be carried out to obtain the length of the anterior commissure-posterior commissure line and its orientation to external bony landmarks. The base of the frame can then be aligned to the plane of the anterior commissure-posterior commissure line. CT guidance is used and can be supplemented with ventriculography. The posterior commissure can be visualized on 2-mm CT slices and used as a reference point.

Physiological corroboration of target tissue localization can be by use of high and low frequency stimulation through a electrode accompanying or incorporated Into the long needle syringe used. A thermistor electrode 1.6 mm in diameter with a 2 mm exposed tip can be used (Radionics, Burlington, Massachusetts). With electrode high frequency stimulation (75 Hz) paraesthetic responses can be elicited in the forearm and hand at 0.5–1.0 V using a Radionics lesion generator (Radionics Radiofrequency Lesion Generator Model RFG3AV). At low frequency (5 Hz) activation or disruption of tremor in the affected limb occurred at 2–3 V. With the methods of the present invention, the electrode is not used to create a lesion. Following confirmation of target tissue localization, a neurotoxin can be injected, thereby causing a reversible, chemical hypothalamectomy. A typical injection is the desired number of units (i.e. about 0.1 to about 5 units of a botulinum toxin type A complex in about 0.01 ml to about 0.1 ml of water or saline. A low injection volume can be uses to minimize toxin diffusion away from target. Typically, the hypothalamic releasing factor or pituitary hormone release inhibition effect can be expected to wear off within about 24 months. Thus, an alternate neurotoxin format, neurotoxin incorporated within a polymeric implant, can be used to provide controlled, continuous release of therapeutic amount of the toxin at the desired location over a prolonged period.(i.e. from about 1 year to about 6 years), thereby obviating the need for repeated toxin injections.

Several methods can be used for stereotactically guided injection of a neurotoxin to various intracranial targets, such as the arcuate nucleus (AN) for treatment of acromegaly. Thus a stereotactic magnetic resonance (MRI) method relying on three-dimensional (3 D) T1-weighted images for surgical planning and multiplanar T2-weighted images for direct visualization of the AN, coupled with electrophysiological recording and injection guidance for AN injection can be used. See e.g. Bejjani, B. P., et al., *Bilateral Subthalamic Stimulation for Parkinson's Disease by Using Three-Dimensional Stereotactic Magnetic Resonance Imaging and Electrophysiological Guidance*, J Neurosurg 92(4); 615–25:2000. The coordinates of the center of the AN can be determined with reference to the patients anterior commissure-posterior commissure line and a brain atlas.

Electrophysiological monitoring through several parallel tracks can be performed simultaneously to define the functional target accurately. The central track, which is directed at the predetermined target by using MRI imaging, can be selected for neurotoxin injection. No surgical complications are expected.

Computer-aided atlas-based functional neurosurgery methodology can be used to accurately and precisely inject the desired neurotoxin or implant a neurotoxin controlled release implant. Such methodologies permit three-dimensional display and real-time manipulation of hypothalamic structures. Neurosurgical planning with mutually preregistered multiple brain atlases in all three orthogonal orientations is therefore possible and permits increased accuracy of target definition for neurotoxin injection or implantation, reduced time of the surgical procedure by decreasing the number of tracts, and facilitates planning of more sophisticated trajectories. See e.g. Nowinski W. L. et al., *Computer-Aided Stereotactic Functional Neurosurgery Enhanced by the Use of the Multiple Brain Atlas Database*, IEEE Trans Med Imaging 19(1);62–69:2000.

Example 2

Treatment of Acromegaly with a Botulinum Toxin

A 55 year old male presents with fatigue, headache, increased sweating, heat intolerance and weight gain. It is determined from a review of photographs supplied by the patient taken over the past 15 years and from the comments of relatives that there has been soft tissue and bone enlargement, with resulting increased hand, foot and hat size, prognathism, enlargement of the tongue, a widening spacing of the teeth and coarsening of facial features. Glucose suppressed GH measured 90 minutes after administration of 100 g glucose is 11 $\mu$g/L and a diagnosis of acromegaly is made. Lack of a pituitary adenoma upon MRI and coned-down x-rays of the sella turcica, and no ectopic GHRH tumors, leads to a conclusion of hypothalamic GHRH excess.

Using CAT scan or MRI assisted stereotaxis, as set forth in Example 1 above, 0.5 units of a botulinum toxin type A (such as BOTOX® or about 2 units of Dysport®) is injected into the arcuate nucleus of the hypothalamus. About one week after surgery, GH in response to glucose suppression has fallen to $<2$ $\mu$g/L and the excess soft tissue begins to recede and disappear. For extended therapeutic relief, a polymeric implants incorporating a suitable quantity of a botulinum toxin type A can be placed at the target tissue site. The implant can comprise a neurotoxin, such as a of botulinum toxin type A, incorporated within biodegradable polymeric microspheres or a biodegradable pellet, either implant format containing about 10 total units (about 0.5 ng) of the type A toxin (i.e. BOTOX®) with implant characteristics of continuous release over a period of at least about four years of a therapeutic level of the toxin at point of the implant release site and for a radius of about 2–3 mm on each side o the target site. The implant can release about 0.5 unit of toxin essentially immediately and further amounts of about 0.5 unit cumulatively over subsequent 24 months periods. The same protocol set forth in this example can be used to treat gigantism with the same primary hypothalamic etiology in adolescents.

Similarly, as an alternative to use of a botulinum toxin type A, from about 5 to about 50 units of a botulinum toxin type B preparation, or from about 0.1 units to about 100 units of a botulinum toxin type $C_1$, D, E, F or G can be stereotactically administered and again, for extended therapeutic relief, one or more polymeric implants incorporating a suitable quantity of a botulinum toxin type B, $C_1$, D, E, F or G can be placed at the target tissue site.

Acromegaly primary to a cholinergically innervated pituitary adenoma can be treated by local administration, or implantation, through transphenoidal surgery of a therapeutically effective amount of a botulinum toxin, as set forth above.

Example 3

Treatment of Hyperthyroidism with a Botulinum Toxin

A 29 year old female with high free thyroxin levels and diffuse goiters with high radioactive uptake, but lacking the eye or skin changes characteristic of Graves' disease is diagnosed with hyperthyroidism due to pituitary hyperplasia. Treatment is by transphenoidal surgery to inject 0.5 units of a botulinum toxin type A (such as BOTOX® or about 2 units of Dysport®) into the anterior pituitary. About one week after surgery, circulating thyroxine levels have returned to normal. For extended therapeutic relief, a polymeric implants incorporating a suitable quantity of a botulinum toxin type A can be placed at the target tissue site.

Similarly, as an alternitive to use of a botulinum toxin type A, from about 5 to about 50 units of a botulinum toxin type B preparation, or from about 0.1 units to about 100 units of a botulinum toxin type $C_1$, D, E, F or G can be administered. For extended therapeutic relief, one or more polymeric implants incorporating a suitable quantity of a botulinum toxin type B, $C_1$, D, E, F or G can be placed at the target tissue site.

Example 4

Treatment of Cushing's Disease with a Botulinum Toxin

A 44-year-old male patient is admitted with symptoms of corticol excess including central distribution of adipose tissue, muscle weakness, purplish striae, hypertension, decreased libido and fatigue, determined to be primary to pituitary overproduction of ACTH. Using CAT scan or MRI assisted stereotaxis, as set forth in Example 1 above, 0.5 units of a botulinum toxin type A (such as BOTOX® or about 2 units of Dysport) is injected into the hypothalamic nucleus responsible for corticotrophin releasing hormone (CRH) production. Altemately, transphenoidal surgery to locally administer the botulinum toxin to the anterior pituitary can be carried out. Within a few days after surgery plasma corticol concentrations fall almost to zero. For extended therapeutic relief, a polymeric implants incorporating a suitable quantity of a botulinum toxin type A can be placed at the target tissue site. The implant can comprise a neurotoxin, such as a of botulinum toxin type A, incorporated within biodegradable polymeric microspheres or a biodegradable pellet, either implant format containing about 10 total units (about 0.5 ng) of the toxin with implant characteristics of continuous release over a period of at least about four years of a therapeutic level of the toxin at point of the implant release site and for a radius of about 2–3 mm on each side o the target site. The implant can release about 0.5 unit of toxin essentially immediately and further amounts of about 0.5 unit cumulatively over subsequent 24 months periods. The same protocol set forth in this example can be used to treat gigantism with the same etiology in adolescents.

Similarly, as an altemative to use of a botulinum toxin type A, from about 5 to about 50 units of a botulinum toxin type B preparation, or from about 0.1 units to about 100 units of a botulinum toxin type $C_1$, D, E, F or G can be stereotactically administered for extended therapeutic relief, one or more polymeric implants incorporating a suitable quantity of a botulinum toxin type B, $C_1$, D, E, F or G can be placed at the target tissue site.

Example 5

Inhibition of Gametoaenesis with Botulinum Toxin Type A

To inhibit ovulation in females or sperm production in males, using CAT scan or MRI assisted stereotaxis, as set forth in Example 1 above, 0.5 units of a botulinum toxin type A, (such as BOTOX® or about 2 units of Dysport® or about 10 units of a botulinum toxin type B) can be is injected into the hypothalamic nucleus responsible for GnRH production. Alternately, transphenoidal surgery to locally administer the botulinum toxin to the anterior pituitary can be carried out to downregulate LH and FSH production. Similarly, a polymeric implant incorporating a suitable quantity of a botulinum toxin type A can be placed at the selected target tissue site. The implant can comprise a neurotoxin, such as a of botulinum toxin type A, incorporated within biodegradable polymeric microspheres or a biodegradable pellet, either implant format containing about 10 total units (about 0.5 ng) of the toxin with implant characteristics of continuous release over a period of at least about four years of a therapeutic level of the toxin at point of the implant release site and for a radius of about 2–3 mm on each side o the target site. The implant can release about 0.5 unit of toxin essentially immediately and further amounts of about 0.5 unit cumulatively over subsequent 2–4 months periods. By this protocol an effective contraceptive method for use In adult males and females is provided.

Example 6

Inhibition of Menstruation with a Botulinum Toxin

To inhibit menstruation, CAT scan or MRI assisted stereotaxis is used, as set forth in Example 1 above, and 0.5 units of a botulinum toxin type A, (such as BOTOX® or about 2 units of Dysport® or about 10 units of a botulinum toxin type B) is injected into the area of the hypothalamic responsible for inhibition of prolactin release from the pituitary, thereby, thereby inducing hyperprolactinemia. Amenorrhea results. Altemately, a polymeric implant incorporating a suitable quantity of a botulinum toxin can be placed at the selected hypothalamic target site, as set forth in Example 5. By this protocol an effective contraceptive method for use in females is provided, as an alternate to the contraceptive method of Example 5 above where ovulation is inhibited by direct inhibition of either or both GnRH and LH and FSH secretion.

Intracranial neurotoxin injection or implantation of a controlled release neurotoxin implant according to the methods of the present invention can be a safe and effective therapy for patients suffering from various endocrine disorders, such as acromegaly, or to achieve contraception. Thus, a method according to the present invention can be used to treat diverse endocrine disorders, including acromegaly, Cushings disease and hyperthyroidism as well as providing effective contraceptive methods.

An intracranial neurotoxin administration method for treating an endocrine disorder according to the invention disclosed herein for has many benefits and advantages, including the following:

1. the symptoms of an endocrine disorder can be dramatically reduced.
2. the symptoms of an endocrine disorder can be reduced for from about two to about four months per injection of neurotoxin and for from about one year to about five years upon implantation use of a controlled release neurotoxin implant.
3. the injected or implanted neurotoxin exerts an intracranial target tissue site specific hypothalamic releasing factor and/or pituitary hormone secretion suppmssant effect.
4. the injected or implanted neurotoxin shows little or no tendency to diffuse or to be transported away from the intracranial injection or implantation site.
5. few or no significant undesirable side effects occur from intracranial injection or implantation of a neurotoxin according to the present invention.
6. the amount of neurotoxin injected intracranially can be considerably less than the amount of the same neurotoxin required by other routes of administration (i.e. intramuscular, intrasphincter, oral or parenteral) to achieve a comparable gonadotrophin suppressant effect.
7. the gonadotrophin suppressant effects of the present methods can result in the desirable side effects of greater patient mobility, a more positive attitude, and an improved quality of life.
8. effective therapeutic doses of a neurotoxin can be delivered to an intracranial target tissue over a prolonged period of time without systemic toxicity.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes intracranial administration methods wherein two or more neurotoxins, such as two or more botulinum toxins, are administered concurrently or consecutively. For example, botulinum toxin type A can be administered intracranially until a loss of clinical response or neutralizing antibodies develop, followed by administration of botulinum toxin type B. Alternately, a combination of any two or more of the botulinum serotypes A–G can be intracranially administered to control the onset and duration of the desired therapeutic result. Furthermore, non-neurotoxin compounds can be intracranially administered prior to, concurrently with or subsequent to administration of the neurotoxin to proved adjunct effect such as enhanced or a more rapid onset of hypothalamic releasing factor or pituitary hormone secretion suppression before the neurotoxin, such as a botulinum toxin, begins to exert its more long lasting suppressant effect.

My invention also includes within its scope the use of a neurotoxin, such as a botulinum toxin, in the preparation of a medicament for the treatment of an endocrine disorder, by intracranial administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating an endocrine condition, the method comprising the step of intracranial administration of a therapeutically effective amount of a botulinum toxin selected from the group consisting of botulinum toxin types A, B, $C_1$, D, E, and G to the hypothalamus or pituitary of a patient, thereby treating a symptom of an endocrine condition by reducing a secretion of a hypothalamic or pituitary hormone or releasing hormone, wherein the endocrine condition is selected form the group consisting of gametogenesis, menstruation, acromegaly, gigantism, Cushing's disease, hypergonadism and hyperthyroidism.

2. The method of claim 1, wherein the botulinum toxin is botulinum toxin type A.

3. The method of claim 1, wherein the botulinum toxin is administered in an amount of between $10^{-2}$ units and 500 units.

4. The method of claim 1, wherein the symptom treating effect persists for between about 1 month and about 5 years.

5. The method of claim 1, wherein the botulinum toxin is administered to the median eminence region of the hypothalamus.

6. The method of claim 1, wherein the botulinum toxin is administered to the anterior pituitary.

7. The method of claim 1 wherein the botulinum toxin is administered to the posterior pituitary.

8. The method of claim 1, wherein the intracranial administration step comprises the step of implantation of a controlled release botulinum toxin system.

9. A method for treating an endocrine condition, the method comprising the step of intracranial administration of a therapeutically effective amount of a botulinum toxin type A to the hypothalamus or pituitary of a patient, thereby alleviating a symptom of an endocrine condition by reducing a secretion of a hypothalamic or pituitary hormone or releasing hormone, wherein the endocrine condition is selected form the group consisting of gametogenesis, menstruation, acromegaly, gigantism, Cushing's disease, hypergonadism and hyperthyroidism.

10. A method for treating an endocrine condition, the method comprising the steps of:

(a) selecting a neurotoxin with hypothalamic releasing hormone suppressant activity:

(b) choosing a hypothalamic target tissue which influences an endocrine disorder; and (c) intracranially administering to the target tissue a therapeutically effective amount of the neurotoxin selected, thereby treating the endocrine condition by reducing a secretion of a hypothalamic releasing hormone, wherein the neurotoxin is a botulinum toxin selected from the group consisting of botulinum toxin types A, B, $C_1$, D, E, and G and wherein the endocrine condition is selected form the group consisting of gametogenesis, menstruation, acromegaly, gigantism, Cushing's disease, hypergonadism and hyperthyroidism.

11. A method for treating hypergonadism, the method comprising the step of in vivo local administration of a therapeutically effective amount of a botulinum toxin type A to a cholinergically influenced hypothalamic tissue to a human patient, thereby alleviating a symptom of hypergonadism in the patient by reducing a secretion of hypothalamic hormone or releasing hormone.

12. A contraceptive method comprising the step of intracranial administration to a hypothalamus or pituitary of a patient of a therapeutically effective amount of a botulinum toxin selected from the group consisting of botulinum toxin types A, B, $C_1$, D, E, and G, thereby reducing a hypothalamic or pituitary secretion of a hormone or releasing hormone required for gametogenesis.

13. The method of claim 12, wherein the botulinum toxin is botulinum toxin type A.

14. A method for inhibiting ovulation, the method comprising the step of intracranial administration to a hypothalamus or pituitary of a patient of a therapeutically effective amount of a botulinum toxin selected from the group consisting of botulinum toxin types A, B, $C_1$, D, E, and G, thereby reducing a hypothalamic or pituitary secretion of a hormone or releasing hormone which influences ovulation.

15. The method of claim 14, wherein the botulinum toxin is botulinum toxin type A.

16. A method for inhibiting sperm production, the method comprising the step of intracranial administration to a hypothalamus or pituitary of a patient of a therapeutically effective amount of a botulinum toxin selected from the group consisting of botulinum toxin types A, B, $C_1$, D, E, and G, thereby reducing a hypothalamic or pituitary secretion of a hormone or releasing which influences sperm production.

17. The method of claim 16, wherein the botulinum toxin is botulinum toxin type A.

* * * * *

UNITED STATES PATENT AND TRADEMARK OFFICE

CERTIFICATE OF CORRECTION

PATENT NO. : 6,827,931 B1
DATED : December 7, 2004
INVENTOR(S) : Donovan

It is certified that error appears in the above-identified patent and that said Letters Patent is hereby corrected as shown below:

Column 1,
Line 10, after "gland", insert -- gland --.
Line 12, after "anterior lobe", replace "adenohypohysis" with -- adenohypophysis --.
Line 24, after "adrenocorticotropin", replace "(corticotropin" with -- (corticotrophin) --.
Line 35, after "and the", replace "parahippocsmpal" with -- parahippocampal --.
Line 41, after "optic chiasma", insert -- , --.
Line 42, after "infundibulum", insert -- , --.
Line 49, before ", dorsomedial", replace "ventmmedial" with -- ventromedial --.
Line 57, after "involved", replace "In" with -- in --.

Column 2,
Line 15, after "and the", replace "adenohypohysis" with -- adenohypophysis --.
Line 29, after "levels", replace "Increased" with -- increased --.
Line 41, after "Potassium", replace "Depoladzation" with -- Depolarization --.
Line 43, after "(8):", replace "268" with -- 2686 --.
Line 49, after "effect", insert -- can --.
Line 51, after "Compensatory", replace "Hypertophy" with -- Hypertrophy --.
Line 52, after "Hypothalamus," replace "Eperientia" with -- Experientia --.

Column 3,
Line 57, after "radiation", replace "Injury" with -- injury --.

Column 4,
Line 25, after "can also", replace "based be" with -- be based --.

Column 6,
Line 61, after "B and $C_1$", replace "is" with -- are --.

Column 7,
Line 3, after "relevant", replace "heurotoxin" with -- neurotoxin --.
Line 5, after "toxin", replace "Is" with -- is --.
Line 12, after "potassium", replace "ation" with -- cation --.
Line 25, after "681:", replace "1897" with -- 1987 --.

Column 8,
Line 14, after "and Use of", replace "Properies" with -- Properties --.
Line 39, after "such", replace "a" with -- as --.
Line 45, before "peptidases", replace "Intracellular" with -- intracellular --.
Line 49, before "known", replace "Is" with -- is --.
Line 59, after "can", insert -- be --.

UNITED STATES PATENT AND TRADEMARK OFFICE
CERTIFICATE OF CORRECTION

PATENT NO. : 6,827,931 B1
DATED : December 7, 2004
INVENTOR(S) : Donovan

It is certified that error appears in the above-identified patent and that said Letters Patent is hereby corrected as shown below:

Column 9,
Line 10, before "stored", replace "Is" with -- is --.
Line 34, after "intramuscular", replace "injectiori" with -- injection --.

Column 10,
Line 1, before "significant", replace "showed" with -- shown --.
Line 9, after "although", replace "R" with -- it --.
Line 15, after "S111-", replace "S11150" with -- S115 --.
Line 16, after "the", replace "Laiyngoscope" with -- Laryngoscope --.
Line 36, after "the", replace "later" with -- latter --.

Column 11,
Lines 12 and 13, before "-Schmiedeberg's", replace "Nauny" with -- Naunyn --.
Line 63, before "system", replace "sympathetic.nervous" with -- sympathetic nervous --.

Column 12,
Line 8, after "such as", replace "such as, adrenal" with -- such as adrenal --.
Line 9, after "cells", insert -- , --.
Line 30, after "membrane", replace "Ion" with -- ion --.
Line 42, after "Pontomesencephalic", replace "Choinergic" with -- Cholinergic --.
Line 63, before "cholinergic", replace "Ch5 Ch6" with -- Ch5-Ch6 --.
Line 65, before "in the midbrain", replace "structure" with -- structures--.

Column 13,
Line 5, after "CRC Press", replace "(19950" with -- (1995) --.
Line 8, before "Central", replace "L" with -- I. --.
Line 12, after "Press", replace "(1 i995)" with -- 1995 --.
Line 13, replace line with -- 136-139 --.
Line 15, after "cholinergic", replace "Innervation" with -- innervation --.
Line 17, after "page", replace "136-136" with -- 136 --.
Line 34, after "there", replace "Is" with -- is --.
Line 58, after "and", replace "In" with -- in --.
Line 64, before "neuroendocrine", replace "an" with -- a --.

Column 14,
Line 14, after "proteins", insert -- . --.
Line 25, after "Clostridium", replace "beratt" with -- beratti --.
Line 67, after "toxin)", replace "toxin)with" with -- toxin) with --.

UNITED STATES PATENT AND TRADEMARK OFFICE
CERTIFICATE OF CORRECTION

PATENT NO. : 6,827,931 B1
DATED : December 7, 2004
INVENTOR(S) : Donovan

It is certified that error appears in the above-identified patent and that said Letters Patent is hereby corrected as shown below:

Column 15,
Line 8, before "invention", replace "present. invention" with -- present invention --.
Line 27, after "native", insert -- neurotoxin --.
Line 29, after "derivative or", replace "or" with -- thereof --.

Column 16,
Line 7, before "lasting", replace "lost" with -- long --.
Line 34, after "prevention", insert -- of --.
Line 37, after "theory", insert -- , --.

Column 17,
Line 2, after "hypothalamus", replace "and or" with -- and / or --.
Line 24, before "Implant", replace "Intersitial" with -- Interstitial --.
Line 39, after "polyanhydride", replace "waters" with -- wafers --.
Line 59, after "Recurrent", replace "Gilomas" with -- Gliomas --.
Line 59, after "Lancet 345:", replace "10081012" with -- 1008 -1012 --.
Line 64, after "then", insert -- be --.

Column 18,
Line 17, after "toxins", insert -- , --.
Line 21, after "brain", replace "barrer" with -- barrier --.
Line 23, after "for use", replace "In" with -- in --.
Line 24, after "09/587250", insert -- , --.
Line 37, after "alia", replace "hypergonadothophism" with -- hypergonadothrophism --.

Column 19,
Line 16, after "tissue involvement", insert -- the tissue -- after "or".
Line 17, after "chosen", insert -- , --.
Line 34, after "delivered", insert -- to --.
Line 40, after "target", insert -- . --.

Column 20,
Line 3, before "a method", replace "Signiflcantly" with -- Significantly --.
Line 9, after "function", replace "Is" with -- is --.
Line 10, before "using", replace "assesses" with -- assessed --.
Line 52, before "to the", replace "approached" with -- approach --.

UNITED STATES PATENT AND TRADEMARK OFFICE
CERTIFICATE OF CORRECTION

PATENT NO. : 6,827,931 B1
DATED : December 7, 2004
INVENTOR(S) : Donovan

It is certified that error appears in the above-identified patent and that said Letters Patent is hereby corrected as shown below:

Column 21,
Line 6, before "(Axon", replace "Micmpositioner" with -- Micropositioner --.
Line 8, after "CRW", replace "sterotaxis" with -- stereotaxis --.
Line 17, after "for a", replace "continuos" with -- continuous --.
Line 26, before "procedures", replace "Sterootactic" with -- Stereotactic --.
Line 30, after "endocrine", insert -- disorder --.
Line 42, before "electrode", replace "a" with -- an --.
Line 58, after "can be", replace "uses" with -- used --.
Line 64, after "release of", insert -- a --.

Column 22,
Line 63, after "polymeric", replace "implants" with -- implant --.
Line 65, after "such as a", delete "of".

Column 23,
Line 6, after "each side", replace "o" with -- of --.
Line 8, after "subsequent", replace "24 months" with -- 2-4 month --.
Line 40, after "polymeric," replace "implants" with -- implant --.
Line 42, after "as an", replace "alternitive" with -- alternative --.

Column 24,
Line 1, after "polymeric", replace "implants" with -- implant --.
Line 4, after "such as a", delete "of".
Line 9, before "point", insert -- the -- before "point".
Line 11, after "side", replace "o" with -- of --.
Line 13, after "subsequent", replace "24" with -- 2-4 --.
Line 28, after "Inhibition of", replace "Gametoaenesis" with -- Gametogenisis --.
Line 35, before "injected", delete "is".
Line 42, after "such as a", delete "of".
Line 48, before "point", insert -- the -- before "point".
Line 49, after "each side", replace "o" with -- of --.
Line 53, after "method for use", replace "In" with -- in --.
Line 65, before "thereby inducing", delete "thereby,".

UNITED STATES PATENT AND TRADEMARK OFFICE

CERTIFICATE OF CORRECTION

PATENT NO. : 6,827,931 B1
DATED : December 7, 2004
INVENTOR(S) : Donovan

It is certified that error appears in the above-identified patent and that said Letters Patent is hereby corrected as shown below:

Column 25,
Line 18, after "herein", delete "for".
Line 26, after "implantation", delete "use".
Line 30, after "secretion", replace "suppmssant" with -- suppressant --.

Column 26,
Line 2, after "neurotoxin", replace "proved" with -- provide --.
Lines 27 and 54, after "selected", replace "form" with -- from --.

Column 27,
Line 3, after "selected", replace "form" with -- from --.

Signed and Sealed this

Thirtieth Day of August, 2005

JON W. DUDAS
*Director of the United States Patent and Trademark Office*